United States Patent
Mawatari et al.

(10) Patent No.: US 12,226,550 B2
(45) Date of Patent: *Feb. 18, 2025

(54) METHOD OF MANUFACTURING A BIOIMPLANT

(71) Applicants: SAGA UNIVERSITY, Saga (JP); KYOCERA CORPORATION, Kyoto (JP)

(72) Inventors: Masaaki Mawatari, Saga (JP); Masatsugu Tsukamoto, Saga (JP); Iwao Noda, Osaka (JP)

(73) Assignees: SAGA UNIVERSITY, Saga (JP); KYOCERA CORPORATION, Kyoto (JP)

( * ) Notice: Subject to any disclaimer, the term of this patent is extended or adjusted under 35 U.S.C. 154(b) by 22 days.

This patent is subject to a terminal disclaimer.

(21) Appl. No.: 18/086,506

(22) Filed: Dec. 21, 2022

(65) Prior Publication Data
US 2023/0121881 A1    Apr. 20, 2023

Related U.S. Application Data

(63) Continuation of application No. 17/080,460, filed on Oct. 26, 2020, now Pat. No. 11,577,006, which is a
(Continued)

(30) Foreign Application Priority Data

Feb. 3, 2012 (JP) .................. 2012-022205

(51) Int. Cl.
A61L 27/32     (2006.01)
A61L 27/54     (2006.01)

(52) U.S. Cl.
CPC ............... *A61L 27/54* (2013.01); *A61L 27/32* (2013.01); *A61L 2300/104* (2013.01); *A61L 2300/404* (2013.01); *A61L 2420/02* (2013.01)

(58) Field of Classification Search
CPC .... A61L 27/54; A61L 27/32; A61L 2300/104; A61L 2300/404; A61L 2420/02
See application file for complete search history.

(56) References Cited

U.S. PATENT DOCUMENTS

| | | |
|---|---|---|
| 5,482,731 A | 1/1996 | Vargas-Gutierrez |
| 5,732,469 A | 3/1998 | Hamamoto et al. |

(Continued)

FOREIGN PATENT DOCUMENTS

| | | |
|---|---|---|
| CA | 2416201 A1 | 1/2003 |
| CN | 1454101 A | 11/2003 |

(Continued)

OTHER PUBLICATIONS

Ding et al. (Surface and Coatings Technology 2003;165:248-257) (Year: 2003).*

(Continued)

*Primary Examiner* — Ernst V Arnold
(74) *Attorney, Agent, or Firm* — Duane Morris LLP

(57) ABSTRACT

Provided is a bioimplant which is capable to inhibit the biofilm formation over a long period of time after an operation. The bioimplant of the present invention comprises a base material of metal, ceramic, or plastic and a thermal spraying film of a calcium phosphate-based material formed at least partially thereon and the silver concentration in the thermal-spray film is 0.05 wt % to 3.00 wt %.

8 Claims, 1 Drawing Sheet

Related U.S. Application Data continuation of application No. 15/405,156, filed on Jan. 12, 2017, now Pat. No. 10,814,039, which is a continuation-in-part of application No. 14/376,183, filed as application No. PCT/JP2013/050661 on Jan. 16, 2013, now abandoned.

(56) References Cited

U.S. PATENT DOCUMENTS

| | | | |
|---|---|---|---|
| 6,113,993 | A | 9/2000 | Gao et al. |
| 6,207,218 | B1 | 3/2001 | Layrolle et al. |
| 6,365,028 | B1 | 4/2002 | Shatrov |
| 6,426,114 | B1 | 7/2002 | Troczynski |
| 6,582,715 | B1 | 6/2003 | Barry et al. |
| 6,994,883 | B2 | 2/2006 | Layrolle et al. |
| 8,821,911 | B2 | 9/2014 | Gan et al. |
| 10,004,604 | B2 | 6/2018 | Hotokebuchi |
| 10,610,614 | B2 | 4/2020 | Hotokebuchi |
| 10,814,039 | B2 * | 10/2020 | Mawatari ........... A61L 27/54 |
| 11,278,642 | B2 | 3/2022 | Hotokebuchi |
| 2001/0024662 | A1 | 9/2001 | Yang |
| 2001/0036530 | A1 | 11/2001 | Noda et al. |
| 2005/0221259 | A1 | 10/2005 | Anderson |
| 2006/0210494 | A1 | 9/2006 | Rabiei et al. |
| 2009/0198344 | A1 | 8/2009 | Prentice et al. |
| 2009/0215009 | A1 | 8/2009 | Noishiki et al. |
| 2009/0280156 | A1 | 11/2009 | Hotokebuchi et al. |
| 2010/0286790 | A1 | 11/2010 | Gruner et al. |
| 2011/0008407 | A1 | 1/2011 | Gan et al. |
| 2013/0138223 | A1 | 5/2013 | Mawatari et al. |
| 2015/0018965 | A1 | 1/2015 | Mawatari |
| 2017/0119932 | A1 | 5/2017 | Mawatari et al. |

FOREIGN PATENT DOCUMENTS

| | | | | |
|---|---|---|---|---|
| EP | 0410711 | A1 | 1/1991 | |
| EP | 1231299 | B1 | 1/2012 | |
| JP | H04-144555 | A | 5/1992 | |
| JP | 2001518827 | A | 10/2001 | |
| JP | 2004503333 | A | 2/2004 | |
| JP | 2005-506879 | A | 3/2005 | |
| JP | 2005097052 | A | 4/2005 | |
| JP | 2005523380 | A | 8/2005 | |
| JP | 2005297435 | A | 10/2005 | |
| JP | 2006151729 | A | 6/2006 | |
| JP | 2008-073098 | A | 4/2008 | |
| JP | 2011-512959 | A | 4/2011 | |
| JP | 2014050610 | A * | 3/2014 | ......... A61C 13/0006 |
| KR | 20060056093 | A | 5/2006 | |
| WO | 1998042390 | A1 | 10/1998 | |
| WO | 1999031303 | A1 | 6/1999 | |
| WO | 2001012883 | A1 | 2/2001 | |
| WO | 2002005862 | A1 | 1/2002 | |
| WO | 03/035123 | A1 | 5/2003 | |
| WO | 2003055449 | A1 | 7/2003 | |
| WO | 2005027801 | A1 | 3/2005 | |
| WO | 2006033956 | A2 | 3/2006 | |
| WO | 2006104628 | A2 | 10/2006 | |
| WO | 2007022211 | A2 | 2/2007 | |
| WO | 2007089894 | A2 | 8/2007 | |
| WO | 2008/029612 | A1 | 3/2008 | |
| WO | 2009053670 | A2 | 4/2009 | |
| WO | 2009/111307 | A2 | 11/2009 | |
| WO | 2012/023510 | A1 | 2/2012 | |

OTHER PUBLICATIONS

English translation of JP2014050610A; 2014: 9 pages. (Year: 2014).*

Sigma Phosphate Buffered Saline ([online] retrieved on Mar. 25, 2024 from https://www.sigmaaldrich.com/US/en/product/sigma/806552; 1 page). (Year: 2024).*

Estridge and Reynolds. Basic Clinical Laboratory Techniques 2011; p. 111 (2 pages). (Year: 2011).

Lee, M.S., Reference Book for Composites Technology vol. 2 1989, CRC Press; p. 82 (Year: 1989).

Ong et al. Critical REviews in Biomedical Engineering 1999;28(5 &6): 1-41 (Year: 1999).

Chai (Dr. Cameron Chai, Hydroxyapatite—Thermal Stability of Synthetic Hydroxyapatites, (Jun. 2002), [Retrieved from internet <URL: . https://www.azom.com/article.aspx?Article1D=1462 >], 3 pages) (Year: 2002).

Chai et al. Hydroxyapatite_13 Thermal Stability of Synthetic Hydroxyapatites (2002) (Source: International Ceramic Monographs, vol. 1, No. 1, pp. 79-85 (1994)) (Year: 2002).

Gross et al., Oxyapatite in hydroxyapatite coatings, Journal of Materials Science, (1998), 33: 3985-3991 (Year: 1998).

Extended European Search Report issued Aug. 6, 2015 in counterpart European Patent Application No. 13743971.7, 7 pages.

International Search Report issued Feb. 4, 2013, in counterpart Japanese Patent Application No. PCT/JP2013/050661, 2 pages (English translation).

International Preliminary Report on Patentability issued Aug. 5, 2014, in counterpart Japanese Patent Application No. PCT/JP2013/050661, 6 pages (English translation).

Noda, et al., "Development of Novel Thermal Sprayed Antibacterial Coating and Evaluation of Release Properties of Silver Ions", Journal of Biomedical Materials Research, Part B: Applied Biomaterials, May 2009, 89(2):456-65 (PubMed, DOI:10.1002/jbm.b.31235).

Shimizaki et al., "In vivo antibacterial and silver-releasing properties of novel thermal sprayed silver-containing hydroxyapatite coating", Journal of Biomedical Materials Research Part B: Applied Biomaterials, 2009, pp. 386-389.

Ando et al., "Development of antibacterial biomaterials", Orthopaedic Surgery and Traumatology, Apr. 2010, 53(5):467-475 (Partial English Translation).

Miyamoto et al, "Development of novel antibacterial biomaterials", Antibiotics & Chemotherapy, 2010, 26(9):125-129 (Partial English Translation).

Noda et al., "Silver-containing hydroxyapatite coating", Journal of Japanese Society for Biomaterials, 2010, 29-4:266-270 (Partial English Translation).

Noda et al., "Development of Thermal Spraying Technique for Silver-Containing Hydroxyapatite (The 4th Report)", The 40th Annual Meeting of the Japanese Society for Replacement Arthroplasty Program/Abstract, 2010, p. 350 (Partial English Translation).

Noda et al., "Development of Thermal Spraying Technique for Silver-Containing Hydroxyapatite (The 5th Report)", The 41st Annual Meeting of the Japanese Society for Replacement Arthroplasty Program/Abstract, 2011, p. 371 (Partial English Translation).

Ando et al., "Development of Silver Antibacterial Biomaterials", The 34th Annual Meeting of the Japanese Society for Study of Bone and Joint Infection Program/Abstract, 2011, p. 64 (Partial English Translation).

Non-Final Office Action issued in corresponding application U.S. Appl. No. 17/080,460 dated Apr. 19, 2022, in 23 pages.

Final Office Action issued in corresponding application U.S. Appl. No. 17/080,460 dated Jul. 27, 2022, in 8 pages.

Gross et al. (J Mater Sci. 1998;33:3985-3991 ). (Year: 1998).

Bai et Bai et al. (J Biomed Mater Res Part B. 2012; 100B:553-561) (Year: 2012).

Iwao Noda et al., "Ginkei Kokin Seitai Zaiiyo no Kaihatsu (1)—Gin Ha Yosha Gijutsu no Kaihatsu to Gin Ion Yoshutsu Tokusei", Japanese Society for Study of Bone and Joint Infections Program Shorokushu, vol. 30, p. 43, 2007; English translation provided.

Chinese Office Action for Application No. 200780033447.7 dated Jan. 11, 2012, English translation provided.

Faust et al., "Biofunctionalised Biocompatible Titania Coatings for Implants", Key Emerging Materials, vols. 206-213, 2002, p. 1547-1550.

Giavaresi et al., "Histomorphometric, ultrastructural and microhardness eveluation of the osseointegration of nanostructured titanium oxide coating by metal-organic chemical vapour deposition: an in vivo study", Biomaterials, vol. 25, 2004, p. 5583-5591.

Japanese Office Action dated Apr. 17, 2012, for Application No. 2006-244479 with the English translation.

(56) References Cited

OTHER PUBLICATIONS

Japanese Office Action dated May 15, 2012, for Application No. 2006-252933 with the English translation.
Lee et al., "Hydroxyapatite-TiO2 Hybrid Coating on Ti Implants", Journal of Biomaterials Applications, vol. 20, Jan. 2006, p. 195-208.
Lin et al., "Characterization of Electrolytic TiO2 Coating on Ti for Biomedical Applications", Journal of the Electrochemical Society, vol. 151, No. 12, 2004, p. D127-D133.
Macionczyk et al., "Repassivationg tantalum/tantalum oxide surface modification on stainless steel implants", Surface and Coatings Technology, vols. 142-144, 2001, p. 1084-1087.
Müller et al., "Surface engineering of Stainless steel materials by covalent collagen immobilization to improve implant biocompatibility", Biomaterials, vol. 26, 2005, p. 6962-6972.
Yao et al., "Anodization: A Promising Nano-Modification Technique of Titanium Implants for Orthopedic Applications", Journal of Nanoscience and Nanotechnology, vol. 6, 2006, 2682-2692.
Yen et al., "Characterization of electrolytic ZrO2 coating on Co-Cr-Mo implant alloys of hip prosthesis", Biomaterials, vol. 22, 2001, p. 125-133.
Ando et al. (In Vitro Antibacterial Properties of Thermal Sprayed Silver-Containing Hydroxyapatite Coating against Methicillin- Resistant *Staphylococcus aureus*, Poster No. 1125, 54th Annual Meeting of the Orthopaedic Research Society, 1 page. Meeting date Mar. 2-5, 2008).
Documentation of meeting date for Ando reference, [Retrieved from internet <URL: http://www.ors.org/past-meetings/>], [Downloaded Sep. 30, 2016], 1 page.
Kofstad et al., Oxidation of titanium in the temperature range of 800-1200 ° C., Journal of the Less Common Metals, Apr. 1961, vol. 3, Issue 2, pp. 89-97, [Retrieved from internet <URL: http://www.sciencedirect.com/science/article/pii/0022508861900017>],Abstract only (2 pages).
Kofstad et al., High-temperature oxidation of titanium, Journal of the Less Common Metals, Jun. 1967, vol. 12, Issue 6, pp. 449-464, [Retrieved from internet <URL: http://www.sciencedirect.com/science/article/pii/0022508867900173 >], Abstract only (2 pages).
Murakami et al. (Evaluation of the structure of Ag in thermal sprayed Ag-containing hydroxyapatite coatings, Journal of the Chemical Society of Japan (2015), 123 (8): 667-671).
Chen et al. (In vitro anti-bacterial and biological properties of magnetron co-sputtered silver-containing hydroxyapatite coating, Biomaterials (on-line Jul. 26, 2006) 27:5512-5517) (6 pages).
Yang et al. (A review on calcium phosphate coatings produced using sputtering process—an alternative to plasma spraying, Biomaterials (2005) 26: 327-337 (cited by Chen, as ref. 39)) (11 pages).
Xue et al. (Effect of hydroxyapatite coating crystallinity on dissolution and osteointegration in vivo, Journal of Biomedical Materials Research Part A (Wiley Interscience, published online Jul. 15, 2005), vol. 74 A, Issue 4, pp. 553-561 ) (9 pages).
Xue bibliographic information for verification of Journal information, [Retrieved from internet <URL: http://onlinelibrary.wiley.com/doi/10.1002/jbm.a.30323/abstract >], (printed Mar. 5, 2016), 3 pages.
Lee et al. (In vitro characterization of postheat-treated plasma-sprayed hydroxyapatite coatings, Surface Coatings & Technology (2005; available on-line Nov. 11, 2004) 197: 367-374), 8 pages.
JP 1994-069582 (machine translation obtained from file wrapper for U.S. Appl. No. 11/816,811, which was published as Noishiki et at., US 2009/0215009 A1) (cited on IOS filed Nov. 23, 2011), 4 pages.
Mukherjee et al. (Antimicrobial activity of aluminium oxide nanoparticles for potential clinical applications (Science against microbial pathogens: communicating current research and technological advances, A. Mendez-Vilas, Ed. (Formatex, 2011), pp. 245-251 [From internet <URL: http://www.formatex.info/microbiology3/book/245-251.pdf ), 7 pages.
Clyne et al. (2.1 Fundamental Studies of the PEO Process (pub. Univ. Cambridge, UK; Composites and Coatings Group, Dept. of Materials Science and Metallurgy) [From internet <URL: http://www.ccg.msm.cam.ac.uk/directory/ research-themes/plasma-electrolytic-oxide-coatings/2.1-fundamental-studies-of-the-peo-process>].
Clyne et al. [Downloaded Feb. 19, 2014], 3 pages.
Keronite PEO (Keronite, What is plasma electrolytic oxidation? [Retrieved from internet <URL: http://www.keronite.com/page-view.php?pagename=What-is-Plasma-Electrolytic-Oxidation? >] [Downloaded Feb. 19, 2014], 1 page).
Keronite Properties (Keronite, General Properties of Keronite Layers, [Retrieved from internet <URL: http://www.keronite.com/page-view.php?pagename=Plasma-Electrolytic-Oxidation-Material-Characteristics >] [Downloaded Feb. 19, 2014], 1 page).
Overgaard et al. (The influence of crystallinity of the hydroxyapatite coating on the fixation of implants: Mechanical and Histomorphometric Result, The Journal of Bone and Joint Surgery, (British Editorial Society of Bone and Joint Surgery, 1999), vol. 81-B, No. 4., pp. 725-731), 7 pages.
Dumbleton et al. (Hydroxyapatite-Coated Prostheses in Total Hip and Knee Arthoplasty, Journal of Joint and Bone Surgery (British) (Nov. 2004) 86 (11): 2526-2540; available from ProQuest), 16 pages.
De Groot et al (Proc Instn Mech Engrs, vol. 212, 1998, pp. 137-147) (Year: 1998).
Johnson et al (The Journal of Infectious Diseases, 1990, vol. 162, pp. 1145-1150, abstract) (Year: 1990).
Uskokovic et al (Biointerphases, May 2019, vol. 14, pp. 1-20) (Year: 2019).

* cited by examiner

METHOD OF MANUFACTURING A BIOIMPLANT

RELATED APPLICATIONS

This application is a continuation of U.S. application Ser. No. 17/080,460, filed Oct. 26, 2020, which is a continuation application of U.S. application Ser. No. 15/405,156, filed Jan. 12, 2017, now U.S. Pat. No. 10,814,039, which is a continuation-in-part of U.S. application Ser. No. 14/376,183 entitled "Bioimplant" filed on Aug. 1, 2014, the contents of each are incorporated herein in its entirety.

BACKGROUND OF THE INVENTION

The present invention relates to an antimicrobial bioimplant.

SUMMARY OF THE INVENTION

Use of bioimplants for treatment of bone injuries/diseases is steadily increasing along with expansion of active and elderly populations. For use as a bone substitute for broken or removed bones or for use as a support to assist a weakened bone, the synthetic bone substitute should form a strong joint or bone together with natural bones and assure the structural integrity thereof. A bone can grow into a neighboring tissue, especially when it is a porous tissue similar to the bone. However, in addition to the growth into porous tissue, the natural bone thus grown into the porous tissue should bind to the bioimplant, forming strong adhesion between them.

An important requirement for fixation of a bioimplant to bone is that the bone grows on and/or into the surface of the bioimplant. Various studies disclose that a calcium phosphate coating on an implant made of cobalt-chromium (Co—Cr) or a titanium (Ti) alloy, for example, a biologic apatite accelerates bone adhesion more quickly than if the implant made of the alloy has a non-coated surface. The biologic apatite $Ca_{10}(PO_4)_6(OH)_2$ is one of the main compounds which constitute human bone and teeth. The synthesized hydroxyapatite (HA) closely resembles a natural apatite and thus has been used in a study in which HA is used in dental and orthopedic implants. An implant has been produced which is easily integrated with neighboring bones and tissues by coating with HA or other crystalline calcium phosphates after transplantation.

However, although use of the synthetic joints in orthopedics for treatment of degenerative joint diseases is a therapeutic treatment effective for reconstruction of joint function, microbes may proliferate on the surface of the synthetic joints, causing post-operative infection. It is because microbes can adhere to the surface of the synthetic joint and the adhered microbes can form a habitat called biofilm. In such a case, antimicrobial agents (antibiotics) are not effective any more, making it difficult to treat the infection. Moreover if myelitis occurs, it is necessary to remove the synthetic joint and repeat the surgery and there may be possibly a case where the infected limb should be ablated.

However, although use of the synthetic joints in orthopedics for treatment of degenerative joint diseases is a therapeutic treatment effective for reconstruction of joint function, microbes may proliferate on the surface of the synthetic joints, causing post-operative infection. It is because microbes can adhere to the surface of the synthetic joint and the adhered microbes can form a habitat called biofilm. In such a case, antimicrobial agents (antibiotics) are not effective any more, making it difficult to treat the infection. Moreover if myelitis occurs, it is necessary to remove the synthetic joint and repeat the surgery and there may be possibly a case where the infected limb should be ablated.

Therefore, there are proposed a method of coating a hydroxyapatite film having high crystallinity and large specific surface area, which is suited for impregnation with an antibiotic, by precipitating hydroxyapatite on the surface of an implant and drying the hydroxyapatite, and a therapeutic agent-impregnated implant in which the coating film is impregnated with the antibiotic (Patent Document 1). The bioimplant prepared by the method is suited for impregnation of antibiotics. However, since the coating film has uniform pore size and porosity, it is difficult to perform sustained release of a medicine at a desired rate and thus the medicine tends to be eluted at a fixed rate at a time.

Alternatively, the applicant proposed a method of controlling the rate of releasing an antibacterial or antimicrobial agent by adjusting the evanescence speed of HA by adjusting the crystallinity of the coating layer of calcium phosphate-based material (Patent Document 2)

PATENT DOCUMENTS

[Patent Document 1] JP-A No. 2005-506879; [Patent Document 2] JP-A No. 2008-73098

DETAILED DESCRIPTION OF THE PREFERRED EMBODIMENTS

Technical Problems to be Solved

Figure 1A:
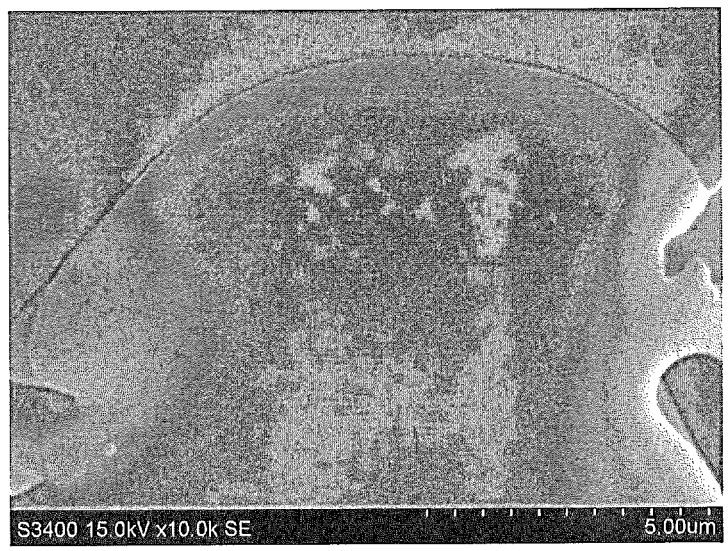
FIG. 1A shows an scanning electron microscope (SEM) image of a surface of the spray coating without carrying out the hydration-treatment.

As described in the above, one of the reasons of post-operative infection is that the microbes form the biofilm on the surface of the implant and this causes the antimicrobial agents to be not effective. Especially, for 24 hours after operation, a risk of the microbial infection is significantly high, because the immune function of a patient is significantly weakened. After that period, the patient slowly recovers own immune function. However, a highly possible state of microbial infection continues over a long period ranging from one week to several weeks after an operation. Especially, a patient having autoimmune disease such as diabetes and further having a weak resistance to the microbial infection (compromised host) has a high risk of microbial infection. Further, a patient who develops infection after implant operation has high infection rates ranging from several times to several tens times in comparison with normal case, when having an operation of replacing implant. Thus, a bioimplant which is capable to inhibit the biofilm formation over a long period of time after an operation is needed. However, it was difficult for the conventional bioimplant to be capable to inhibit the biofilm formation over such a long period of time.

Thus, an object of the present invention is to provide a bioimplant which is capable to inhibit the biofilm formation over a long period of time after an operation.

Means to Solve the Problems

The bioimplant according to the present invention, which was made to overcome the problems above, is characterized in that it comprises a base material of metal, ceramic or plastic and a thermal spraying film made of a calcium phosphate-based material formed at least partially thereon, the silver concentration in the thermal spraying film being 0.05 wt % to 3.00 wt %.

In the present invention, the calcium phosphate-based material is preferably a compound or a mixture of two or more compounds selected from the group consisting of hydroxyapatite, α-tricalcium phosphate, β-tricalcium phosphate, and tetracalcium phosphate.

Effect of the Invention

Since the bioimplant of the present invention can inhibit the biofilm formation over a long period of time after an operation, a curative effect of antimicrobial agents on infection can be maintained, and thereby decreasing risk of post-operative infection. Further, as used herein, "long period of time" refers to a period in which the risk of the post-operative infection is high, and the period ranges from one week to several weeks after an operation.

BEST MODE FOR CARRYING OUT THE INVENTION

Hereinafter, favorable embodiments of the present invention will be described in detail.

The bioimplant according to the present invention is a bioimplant, comprising a base material of metal, ceramic, or plastic and a thermal spraying film made of a calcium phosphate-based material formed at least partially thereon, the silver concentration in the thermal spraying film being 0.05 wt % to 3.00 wt %.

The bioimplant according to the present invention include metal, ceramic, and plastic implants, such as synthetic bones and fixation devices used for treatment of diseases and injuries, synthetic joints used for reconstruction of lost joint function, and synthetic tooth roots used for reconstruction of teeth.

A metal, ceramic, or plastic material may be used as the base material of the bioimplant. A stainless steel alloy, a cobalt-chromium alloy, titanium, a titanium alloy, alumina, zirconia or the like may be used as the metal, but titanium and titanium alloys are preferable. The titanium alloys for use include alloys of titanium with at least one metal selected from aluminum, tin, zirconium, molybdenum, nickel, palladium, tantalum, niobium, vanadium, platinum and the like. Preferably, it is Ti-6Al-4V alloy. Alternatively, the ceramics for use include, for example, alumina, zirconia, composite alumina-zirconia ceramics and the like. Yet alternatively, the plastics for use include, for example, polyethylenes, fluorine resins, epoxy resins, PEEK resins, Bakelite and the like.

The calcium phosphate-based material for use may be a compound or a mixture of two or more compounds selected from the group consisting of hydroxyapatite, α-tricalcium phosphate, β-tricalcium phosphate, and tetracalcium phosphate. It is preferably hydroxyapatite.

(Production Method)

The thermal spraying methods used for forming a thermal spraying film of a calcium phosphate-based material include flame spraying method, high-speed flame spraying method, plasma spraying method, and cold spraying method. For example in the case of the flame spraying method, a film is formed on the surface of a base material by melting a thermal spraying material or bringing it close to the melting state by placing it in a gas flame generated with oxygen and a flammable gas and spraying the resulting thermal spraying material on the base material. In the case of the normal flame spraying method, the thermal spraying temperature is about 2700° C. and the thermal spraying speed is Mach 0.6. Under normal thermal spraying condition, for example, a thermal spraying powder can be fed with 100 psi dry air into a gas frame torch generated with 50 psi oxygen gas and 43 psi acetylene gas and the resulting powder can be thermally sprayed at a thermal spraying distance of 60 to 100 μmm.

The thickness of the thermal spraying film is 5 to 100 μm, preferably 20 to 40 μm, since it is not possible to cover the thermal spraying area entirely when the thickness is less than 5 μm and the adhesion strength of the film declines because of the residual stress during thermal spraying when the thickness is more than 100 μm.

It is preferable to carry out a heat-treatment of the prepared thermal spraying film. The heat-treatment can increase the crystallinity of a calcium phosphate-based material, and thereby improving the stability of the film. The heat-treatment may be carried out at a temperature range of 400 to 1000° C. for 0.5 to 7 hours under the reduced pressure of 10-Pa or less. It is preferable to carry out at a temperature range of 550 to 850° C. for 1 to 5 hours.

Figure 1B:
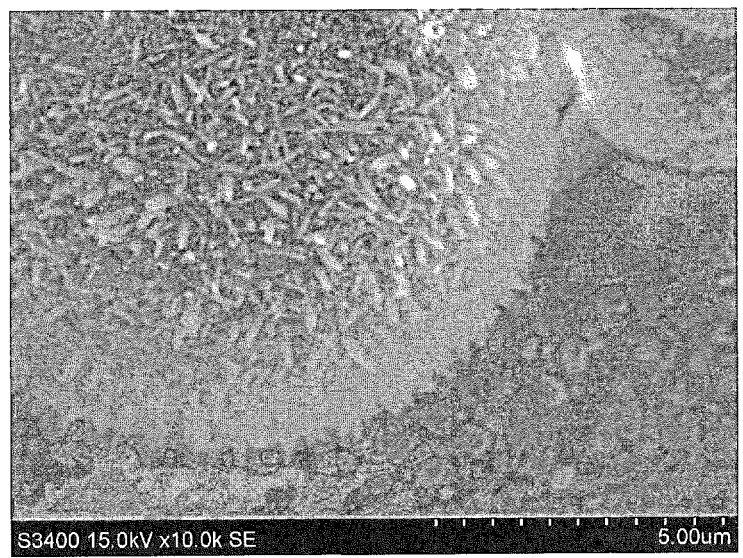
FIG. 1B shows an SEM image of the surface of a spray coating after carrying out the hydration-treatment.

Further, it is preferable to carry out a hydration-treatment of the prepared thermal spraying film after carrying out the heat-treatment. The hydration-treatment can convert oxyapatite to hydroxyapatite, and results in fine crystals of calcium phosphate being formed (e.g., separated out from the coating and/or deposited/precipitated) on the surface of the coating, thereby stabilizing an elution property of silver ion. As used herein, "separated out" refers to a process in which an insoluble crystalized material is exposed or separated, whereas a soluble material is dissolved. Also, as used herein, "deposited/precipitated" refers to a process in which new crystals are generated and accumulated on the surface of a coating. The formation of fine crystals of calcium phosphate on the surface of the coating stabilizes the elution property of silver ions because the fine crystals cover the surface of the coating, which reduces the rate of elution of silver ions. The hydration-treatment includes a step of adding water molecule to material and may be carried out, for example, by immersing the thermal spraying film in water at a temperature of 60-100° C. for 10-60 μminutes, in accordance with some embodiments. FIG. 1A shows an scanning electron microscope (SEM) image of a surface of the spray coating without carrying out the hydration-treatment and FIG. 1B shows an SEM image of the surface of spray coating after carrying out the hydration-treatment. As shown in FIG. 1B, it is observed that needle-shaped crystals, plate-shaped crystals, and/or granular-shaped crystals are formed on the surface of the coating. In some embodiments, the size of the crystals in length, width or thickness is in the range of approximately 0.01 to 2.00 μmicrometers (m).

It is possible to control the silver concentration in the thermal spraying film by adjusting the amount of the raw silver material blended to the thermal spraying material, i.e., the calcium phosphate-based material. The silver concentration in the thermal spraying film is 0.05 wt % to 3.00 wt %, preferably 0.05 wt % to 2.50 wt %, more preferably 0.05 wt % to 1.00 wt %, and more preferably 0.1 wt % to 1.00 wt %. It is because the antimicrobial action is not sufficient when the silver concentration is less than 0.05 wt %. Alternatively when it is more than 3.00 wt %, the implant may become toxic to tissues and organs in the body. According to literature, use of a great amount of silver leads to Argylia disease (disease leading to graying in color of the entire skin), decrease of leucocytes, and damage to liver and kidney. Our studies also showed that there are deformation of cells and inhibition of neonatal bone formation when the silver concentration is more than 3.00 wt %.

An example of the bioimplant according to the present invention is a synthetic joint consisting of a stem which is a bone contact portion inserted into the bone and a neck unit formed on the top end of the stem for fixation of bone head ball, wherein at least part of the bone contact portion is covered with a thermal spraying film of a calcium phosphate-based material and the silver concentration in the thermal-spray film is 0.05 wt % to 3.00 wt %. The synthetic joint is preferably made of titanium or a titanium alloy.

Examples—Experiment 1 (Sample Preparation)

Hydroxyapatite containing a particular amount of silver oxide was sprayed onto one side of a pure titanium plate with a size of 50 μmm×50 μmm×2 μmm by flame spraying method, to form a thermal-spray film having a thickness of about 40 μm. The flame spraying was carried out by introducing, with 100 psi dry air, the thermal spraying powder into a gas frame torch generated with 50 psi oxygen gas and 43 psi acetylene gas and spraying the fused powder at a thermal spraying distance of 60 to 100 μmm.
(Measurement of Silver Concentration)

After sufficient drying at 100° C., each sample was weighed and then dissolved in a nitric acid solution (5 μmL of nitric acid and 50 mL of purified water) while heating. The silver concentration in the film was determined by measuring the silver concentration in the solution quantitatively by ICP emission spectrophotometric analysis. Then, the sample after removal of the film by solubilization was dried sufficiently and weighed again, and the film weight was calculated from the difference in weight from the sample before solubilization. The silver concentration in film (wt %) was calculated by dividing the amount of silver in film by the weight of the film. The silver concentration of the film in this experiment was 0.3 wt %.
(Test for Antimicrobial Activity)

As a test for antimicrobial activity, an evaluation of performance of inhibiting biofilm formation was carried out. Methicillin-resistant Staphylococcus aureus was adhered to samples, and then the samples was immersed in a fetal bovine serum retained at a temperature of 37° C. and was cultivated under flow condition by stirring at 60 rpm. After culture for one week and two weeks, biofilm formed on the film was stained by fluorescent staining and biofilm coverage on the film was determined and morphology thereof observed by fluorescence microscope. Further, the biofilm coverage was determined from a surface area ratio of a fluorescence emission area obtained by using image analysis software.

Experiment 2

A sample was prepared in a similar manner with experiment 1 except that Hydroxyapatite containing no silver oxide was used, and supplied to the test for antimicrobial activity.
(Result)

Table 1 shows the biofilm coverage. The biofilm coverage of the samples of one-week culture and two-week culture in the experiment 1 became lower than those of the control samples, indicating that the samples of the experiment 1 shows inhibiting the biofilm formation.

TABLE 1

| | Biofilm coverage (%) | |
|---|---|---|
| | After culture for 1 week | After culture for 2 weeks |
| Experiment 1 | 1.3 | 29.9 |
| Experiment 2 | 5.7 | 48.9 |

Experiment 3

This experiment was carried out to reconfirm the effect of the silver concentration in the film, and the samples having silver concentrations of 0, 0.05, 0.1, 0.3 wt % were prepared.
(Sample Preparation)

Hydroxyapatite containing a particular amount of silver oxide was sprayed onto one side of a pure titanium plate with a diameter of 14 μmm and a thickness of 1 μmm by flame spraying method, to form a thermal-spray film having a thickness of about 40 μm. The samples having silver concentrations of 0, 0.05, 0.1, 0.3 wt % were prepared by adjusting the amount of the silver oxide blended to the thermal spraying material, The flame spraying was carried out in a similar manner as described in Experiment 1.
(Measurement of Silver Concentration)

The measurement of silver concentration was carried out in a similar manner as described in Experiment 1.
Test for Antimicrobial Activity)

As a test for antimicrobial activity, a test of inhibiting biofilm formation was carried out. The test was carried out in a similar manner as described in Experiment 1 except that a culture medium was replaced every fourth day to avoid the culture medium of fetal bovine serum from being saturated with a bacteria.
(Result)

Table 2 shows the results of measurements of the biofilm coverage. The biofilm coverage of the samples of one-week culture and two-week culture in this experiment became lower in proportion to the silver concentration in the film. This indicated that biofilm formation is inhibited as the silver concentration in the film increases. Further, considering the results of this experiment and empirical knowledge on the bacterial growth, it is estimated that the samples maintain an effect of inhibiting biofilm formation for a long period time, such as about four weeks when the silver concentration is 0.05%, about six weeks when the silver concentration is 0.1%, and about ten weeks when the silver concentration is 0.3%.

TABLE 2

| Silver | Biofilm coverage (%) | |
|---|---|---|
| concentration in film (wt %) | After one-week culture | After two-week culture |
| 0 | 28.6 | 55.0 |
| 0.05 | 7.5 | 37.1 |
| 0.1 | 5.3 | 21.4 |
| 0.3 | 3.6 | 9.3 |

Since the bioimplant of the present invention is capable to inhibit the biofilm formation over a long period of time after an operation, the risk of post-operative infection can be significantly decreased. Especially, a large effect can be expected when applying to patients having high risk of infection, for example, to a compromised host or a patient who develops infection after implant operation and have an operation of replacing implant.

The foregoing outlines features of several exemplary embodiments of the invention so that those of ordinary skill in the art may better understand the aspects of the invention. Those skilled in the art will appreciate that they may readily use the present disclosure to make various changes, substitutions, and alterations to the embodiments disclosed herein to arrive at equivalent structures that are encompassed within the scope of the present invention. Thus, the scope of the invention should not be limited by the exemplary embodiments disclosed herein but rather the scope of the invention should be commensurate with the plain meaning of the claims issued from the present disclosure.

What is claimed is:

1. A method of manufacturing a bioimplant, comprising:
   providing a base material of the bioimplant;
   forming a coating comprising a calcium phosphate-based material and a silver material on at least a part of a surface of the base material;
   after forming the coating, heating the coating at a predetermined temperature under a predetermined pressure to form oxyapatite in the coating; and
   immersing the coating in purified water to convert oxyapatite present in the coating to hydroxyapatite, wherein the immersing results in fine crystals of the hydroxyapatite being formed on a surface of the coating, wherein a size of the fine crystals of hydroxyapatite is in a range of 0.01 μm to 2.00 μm in length, thickness or width, and
   wherein a temperature of the purified water is in a range of 60 to 100 degrees Celsius.

2. The method according to claim 1, wherein said calcium phosphate-based material is a compound or a mixture of two or more compounds selected from the group consisting of hydroxyapatite, alpha-tricalcium phosphate, beta-tricalcium phosphate, and tetracalcium phosphate.

3. The method according to claim 1, wherein the base material comprises a metal.

4. The method according to claim 1, wherein the base material comprises ceramic.

5. The method according to claim 1, wherein the base material comprises a plastic.

6. The method according to claim 1, wherein:
   the heating is performed at a temperature range of 550 to 850 degrees Celsius for a period of time in the range of 1 to 5 hours; and
   the immersing is performed for a period of time in the range of 10 to 60 μminutes.

7. The method according to claim 1, wherein the resulting coating comprises a silver concentration in the range of 0.05 wt % to 3.00 wt %.

8. The method according to claim 1, wherein the forming the coating is performed by applying a thermal sprayed film comprising a calcium phosphate-based material and a silver material.

* * * * *